US009259176B2

(12) United States Patent
Suzuki

(10) Patent No.: US 9,259,176 B2
(45) Date of Patent: Feb. 16, 2016

(54) BIOLOGICAL OPTICAL MEASUREMENT INSTRUMENT AND OPERATION METHOD THEREFOR

(75) Inventor: Hiromichi Suzuki, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 311 days.

(21) Appl. No.: 13/880,744

(22) PCT Filed: Nov. 2, 2011

(86) PCT No.: PCT/JP2011/075253
§ 371 (c)(1),
(2), (4) Date: Apr. 22, 2013

(87) PCT Pub. No.: WO2012/066930
PCT Pub. Date: May 24, 2012

(65) Prior Publication Data
US 2013/0211218 A1 Aug. 15, 2013

(30) Foreign Application Priority Data

Nov. 16, 2010 (JP) ................................. 2010-256190

(51) Int. Cl.
| A61B 5/1455 | (2006.01) |
| G01J 3/10 | (2006.01) |
| G01J 3/28 | (2006.01) |
| G01J 3/42 | (2006.01) |
| A61B 5/145 | (2006.01) |
| G01N 21/31 | (2006.01) |
| G01N 21/359 | (2014.01) |

(52) U.S. Cl.
CPC ........... *A61B 5/14552* (2013.01); *A61B 5/1455* (2013.01); *A61B 5/14546* (2013.01); *G01J 3/10* (2013.01); *G01J 3/28* (2013.01); *G01J 3/42* (2013.01); *A61B 2560/0252* (2013.01); *A61B 2560/0437* (2013.01); *G01N 21/359* (2013.01); *G01N 2021/3133* (2013.01); *G01N 2021/3144* (2013.01); *G01N 2021/3155* (2013.01)

(58) Field of Classification Search
CPC ............. A61B 5/1455; A61B 5/14551; A61B 5/14552
See application file for complete search history.

(56) References Cited

U.S. PATENT DOCUMENTS 6,011,986 A * 1/2000 Diab et al. .................... 600/323

* cited by examiner

*Primary Examiner* — Eric Winakur
(74) *Attorney, Agent, or Firm* — Oliff PLC

(57) ABSTRACT

A biological optical measurement instrument includes a single temperature sensor that detects a radiation temperature from a plurality of light emitting elements that emit light of a predetermined wavelength, and an absorption coefficient correcting unit that corrects an absorption coefficient value of a notable substance inside the object on the basis of the radiation temperature detected by the temperature sensor, referring to data indicating a correspondence relationship between a temperature obtained in advance for each emitted light of the plurality of light emitting elements and an absorption coefficient value that varies according to the temperature.

8 Claims, 15 Drawing Sheets

FIG. 8

| | WAVELENGTH VALUE OF 695 nm [nm] | | | WAVELENGTH VALUE OF 830 nm [nm] | |
|---|---|---|---|---|---|
| | INITIAL VALUE | CURRENT VALUE | | INITIAL VALUE | CURRENT VALUE |
| No.1 | 695.2 | 698.2 | No.9 | 830.0 | 833.0 |
| No.2 | 696.3 | 699.3 | No.10 | 831.3 | 834.3 |
| No.3 | 694.8 | 697.8 | No.11 | 829.7 | 832.7 |
| No.4 | 695.0 | 698.0 | No.12 | 830.4 | 833.4 |
| No.5 | 693.9 | 696.9 | No.13 | 835.7 | 838.7 |
| No.6 | 697.1 | 700.1 | No.14 | 834.8 | 837.8 |
| No.7 | 695.5 | 698.5 | No.15 | 830.0 | 833.0 |
| No.8 | 695.0 | 698.0 | No.16 | 829.9 | 832.9 |

| REFERENCE TEMPERATURE | | 20 |
|---|---|---|
| TEMPERATURE IN MEASUREMENT | No.1 | 40 |
| WAVELENGTH VARIATION | No.1 | 3 |

FIG. 15

| | WAVELENGTH VALUE OF 695 nm [nm] | | | | WAVELENGTH VALUE OF 830 nm [nm] | |
|---|---|---|---|---|---|---|
| | INITIAL VALUE | CURRENT VALUE | | | INITIAL VALUE | CURRENT VALUE |
| No.1 | 698.2 | 699.2 | | No.9 | 833.0 | 834.0 |
| No.2 | 699.3 | 700.3 | | No.10 | 834.3 | 835.3 |
| No.3 | 697.8 | 698.8 | | No.11 | 832.7 | 833.7 |
| No.4 | 698.0 | 699.0 | | No.12 | 833.4 | 834.4 |
| No.5 | 696.9 | 697.9 | | No.13 | 838.7 | 839.7 |
| No.6 | 700.1 | 701.1 | | No.14 | 837.8 | 838.8 |
| No.7 | 698.5 | 699.5 | | No.15 | 833.0 | 834.0 |
| No.8 | 698.0 | 699.0 | | No.16 | 832.9 | 833.9 |

| | | |
|---|---|---|
| OPTICAL OUTPUT [mW] | | 30 |
| OPTICAL OUPUT IN ADJUSTMENT [mW] | No.1 | 40 |
| WAVELENGTH VARIATION [nm] | No.1 | 1 |

US 9,259,176 B2

BIOLOGICAL OPTICAL MEASUREMENT INSTRUMENT AND OPERATION METHOD THEREFOR

TECHNICAL FIELD

The present invention relates to a biological optical measurement instrument that irradiates a living body with near infrared rays and detects light passed through the inside of the living body or reflected by the inside of the living body to measure blood circulation, hemodynamics and a variation of hemoglobin (hereinafter, abbreviated as Hb) inside the living body, and to an operation method therefor.

BACKGROUND ART

A biological optical measurement instrument is a device that is capable of irradiating a living body with near infrared rays and detecting light passed through the inside of the living body or reflected by the inside of the living body to simply measure blood circulation, hemodynamics and a variation of Hb inside the living body with less restraint and non-invasiveness to an object. In recent years, a technique that images measured data obtained from a plurality of measurement regions of a living body using a multi-channel device has been realized, and is expected to be applied to clinical tests.

In the biological optical measurement instrument, a semiconductor laser (hereinafter, abbreviated as LD) for emission of near infrared rays is used. It is known that the LD has temperature dependency on electric characteristics (threshold current, driving voltage and the like) or optical characteristics (optical output, wavelength and the like).

In the biological optical measurement instrument, a living body is irradiated with near infrared rays of a predetermined output, and a variation of Hb is calculated by light passed through the inside of the living body or reflected by the inside of the living body and an absorption coefficient value of Hb in blood. The absorption coefficient value of Hb in blood varies according to a wavelength value of the near infrared rays. Thus, if electric characteristics and optical characteristics vary according to a temperature change in an LD, the wavelength value of the near infrared rays varies, and thus, the absorption coefficient value of Hb also varies, which affects detection of the variation of Hb.

In this regard, PTL 1 discloses a technique that controls a driving voltage according to a driving current of an LD to stabilize a wavelength of the LD. PTL 2 discloses a technique that corrects a temperature of an LD using a Peltier element to reduce a wavelength variation.

PTL 3 discloses a technique that corrects a parameter such as an absorption coefficient value of Hb according to a temperature change in an LD in a calculation process of the concentration of oxy Hb or deoxy Hb in an optical measuring device such as an oxygen monitor to correct a wavelength variation due to the temperature change in the LD.

CITATION LIST

Patent Literature

[PTL 1] JP-A-2006-114774
[PTL 2] JP-A-2008-235683
[PTL 3] JP-A-2000-193585

SUMMARY OF INVENTION

Technical Problem

In the biological optical measurement instrument, in order to irradiate a plurality of measurement regions inside an object with light at a time, a plurality of (for example, 16 to 80) LDs are arranged in a casing. The temperature of the LDs shows distribution according to arrangement positions of the LDs in the casing. Thus, in order to stabilize the wavelength value of the LD in the techniques of PTL 1 and PTL 2, a control circuit of a driving voltage and a Peltier element are necessary for each LD, which increase a circuit size and a device size and increase power consumption.

Further, in order to apply the technique that detects the temperature in the LD and corrects the parameter such as an absorption coefficient value in the calculation as in PTL 3 to a biological optical measurement instrument, it is necessary to respectively arrange the temperature detection elements in the plurality of LDs of the biological optical measurement instrument and to correct the parameter in the calculation for each LD according to the detected temperature, which complicates the device and the calculation process.

An object of the invention is to provide a biological optical measurement instrument that is capable of simply obtaining a measurement result in which a wavelength variation of a semiconductor laser is corrected, and an operation method therefor.

Solution to Problem

According to an aspect of the invention, in order to achieve the above-described objects, there is provided a biological optical measurement instrument including: a single temperature sensor that detects a radiation temperature from a plurality of light emitting elements that emit light of a predetermined wavelength; and an absorption coefficient correcting unit that corrects an absorption coefficient value of a notable substance inside the object on the basis of the radiation temperature detected by the temperature sensor, referring to data indicating a correspondence relationship between a temperature obtained in advance for each emitted light of the plurality of light emitting elements and an absorption coefficient value that varies according to the temperature.

Advantageous Effects of Invention

According to the invention, it is possible to provide a biological optical measurement instrument that is capable of simply obtaining a measurement result in which a wavelength variation of a semiconductor laser is corrected, and an operation method therefor.

BRIEF DESCRIPTION OF DRAWINGS

FIG. 3 shows an external appearance in a state where a side panel and a rear panel of a casing of the biological optical measurement instrument in FIG. 1 are removed, in which FIG. 3(a) is a side view, and FIG. 3(b) is a rear view.

FIG. 8 is a table illustrating an oscillation wavelength of each LD obtained in the first embodiment.

FIG. 15 is a table illustrating an oscillation wavelength of each LD obtained in the third embodiment.

DESCRIPTION OF EMBODIMENTS

Hereinafter, a biological optical measurement instrument according to an embodiment of the invention will be described.

First Embodiment

The biological optical measurement instrument of the invention overlaps near infrared rays of two wavelengths with which a measurement portion in the vicinity of the surface of a living body is irradiated, and detects the intensities of reflected light in the measurement portion and transmitted light of a measurement point (hereinafter, simply referred to as transmitted light), and then, blood circulation, hemodynamics and a variation of Hb in the measurement portion are calculated by a calculation process.

Figure 1:
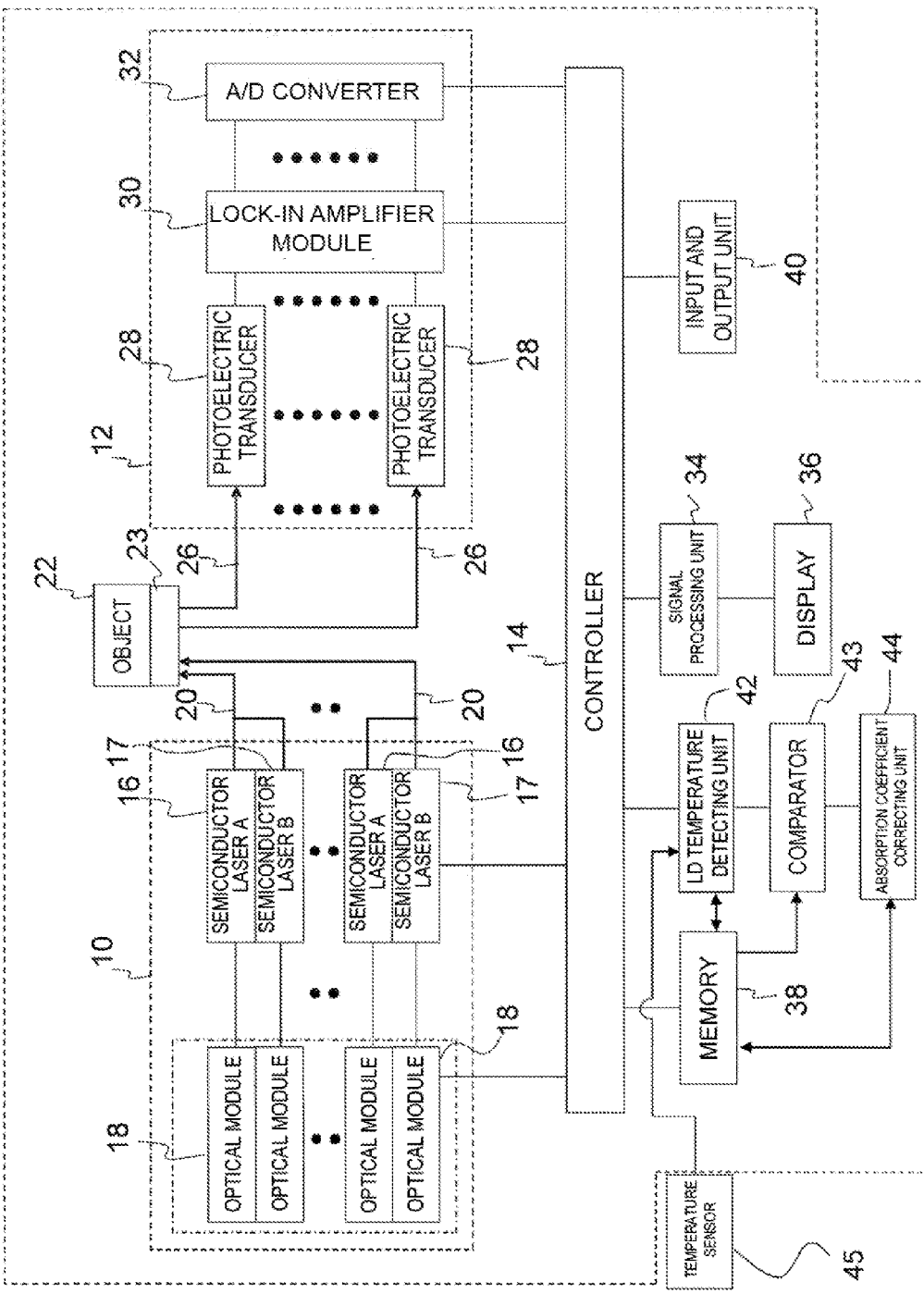
FIG. 1 is a block diagram illustrating a configuration of a biological optical measurement instrument according to a first embodiment.

As shown in FIG. 1, the biological optical measurement instrument includes a light source 10 that radiates near infrared rays, an optical measurement unit 12 that measures transmitted light in the measurement portion and converts the measured light into an electric signal, a controller 14 that controls driving of the light source 10 and the optical measurement unit 12, a signal processing unit 34, a display 36, an input and output unit 40, an LD temperature detecting unit 42, a memory 38, a comparator 43, an absorption coefficient correcting unit 44, and a temperature sensor 45 that converts a temperature of a thermistor or the like into an electric signal for output.

The light source 10 includes a plurality of semiconductor lasers A (hereinafter, simply referred to as LDA) 16 that emits light of a first predetermined wavelength (for example, 695 nm), a plurality of semiconductor lasers B (hereinafter, simply referred to as LDB) 17 that emits light of a second wavelength (for example, 830 nm) that is different from the first wavelength, optical modules 18 that are respectively connected to the LDAs 16 and the LDBs 17, and a plurality of irradiation optical fibers 20.

The optical modules 18 supply a driving current to the LDAs 16 and the LDBs 17, respectively. Further, one LDA 16 and one LDB 17 are used as a single set, the driving currents of the LDA 16 and the LDB 17 are modulated, and the intensities of output laser beams for each set are modulated at predetermined different frequencies.

Beams emitted from one set of the LDA 16 and the LDB 17 are incident onto an incident end of the same optical fiber 20 to be overlapped with each other, and are propagated through the irradiation optical fiber 20. Exiting ends of the irradiation optical fibers 20 of the respective sets are fixed to a probe holder 23 in a predetermined arrangement. The probe holder 23 is mounted to an object 22, and the exiting ends of the irradiation optical fibers 20 are disposed at irradiation positions in the vicinity of a plurality of measurement points in a measurement portion (for example, head portion) of the object. Thus, the measurement points of the object 22 are irradiated the laser beams of two wavelengths that are modulated at the predetermined frequencies and are overlapped with each other.

In FIG. 1, although all of the LDAs 16 and the LDBs 17 are not shown, total 16 to 80 LDAs 16 and LDBs 17 are mounted in a real biological optical measurement instrument.

Wavelengths of the beams of the LDAs 16 and the LDBs 17 are selected according to spectral characteristics of a notable substance in a living body. In a case where oxygen saturation or blood volume is measured from the concentrations of deoxy Hb and oxy Hb, one or plural wavelengths are selected for use from beams in a wavelength range of 600 nm to 1400 nm.

The optical measurement unit 12 includes a plurality of detection optical fibers 26, a plurality of photoelectric transducers 28 such as a photodiode, a lock-in amplifier 30, and an A/D converter 32. The number of the detection optical fibers 26 is equal to or more than the number of the irradiation optical fibers 20. Incident ends of the detection optical fibers 26 are fixed to the probe holder 23 in a predetermined arrangement, and are disposed at detection positions in the vicinity of the plurality of measurement points in the measurement portion of the object. Beams which irradiate from the irradiation optical fibers 20 and has passed through the vicinity of the surface of the object are incident onto the incident ends of the detection optical fibers 26.

Accordingly, regions between the exiting ends of the irradiation optical fibers 20 and the incident ends of the detection optical fibers 26 correspond to the measurement points.

Beams incident onto the detection optical fibers 26 are propagated by the detection optical fibers 26 up to the photoelectric transducers 28, and are detected by the photoelectric transducers 28. The lock-in amplifier module selectively detects a frequency modulated signal for each set of the LDA 16 and the LDB 17 from electrical signals output by the photoelectric transducers 28, to thereby selectively detect a frequency modulated signal corresponding to a measurement point. Thus, it is possible to obtain detection signals of a wavelength of LDA 16 and a wavelength of LDB 17 for each region (measurement point) between the light irradiation position and the detection position. That is, it is possible to obtain detection signals of a channel number corresponding to two times the number of the measurement points. The A/D converter 32 converts an output signal of the lock-in amplifier 30 into a digital signal. In FIG. 1, although all of the photoelectric transducers 28 are not shown, the photoelectric transducers 28 having the same number as that of the optical fibers 26 are mounted in a real device.

The signal processing unit 34 processes an output of the A/D converter 32, calculates a concentration change or the like of the notable substance in the living body, and creates a graph showing a calculation result for each channel or an image of the object obtained by plotting the graph on a two-dimensional image. In the present embodiment, an oxyhemoglobin (oxy Hb) concentration change, a deoxyhemoglobin (deoxy Hb) concentration change, and an entire hemoglobin (entire Hb) concentration change are calculated using a laser beam of 695 nm and a laser beam of 830 nm. The display 36 displays a processing result of the signal processing unit 34. The memory 38 stores data necessary for the process of the signal processing unit 34 and the processing result. The input and output unit 40 receives inputs of various commands necessary for the operation of the device from an operator. The controller 14 controls the respective units in light irradiation and detection, and signal processing and display.

Next, a method of calculating the oxy Hb concentration change, the deoxy Hb concentration change and the entire Hb concentration change according to the modified Lambert-Beer's law in the calculation process of the signal processing unit 34 will be described.

A relational expression between the oxy Hb concentration change and the deoxy Hb concentration change, and a light intensity change in blood when a beam of a wavelength of $\lambda$ is incident may be expressed as the following Expression (1). In Expression (1), it is assumed that an absorbance change is $\Delta A(\lambda)$, light intensities (detection light intensities) before and after change are respectively Ibase($\lambda$) and Iact($\lambda$), absorption coefficient values of oxy Hb and deoxy Hb are respectively $\epsilon o(\lambda)$ and $\epsilon d(\lambda)$, an oxy Hb variation and a deoxy Hb variation are respectively $\Delta(CoL)$ and $\Delta(CdL)$, an optical path length L is constant, and a dissipation term is negligibly small.

[Expression 1]

$$\Delta A(\lambda) = -\ln\left(\frac{I_{act}(\lambda)}{I_{base}(\lambda)}\right) = \varepsilon_o(\lambda)\Delta(C_oL) + \varepsilon_d(\lambda)\Delta(C_dL) \quad (1)$$

Figure 2:
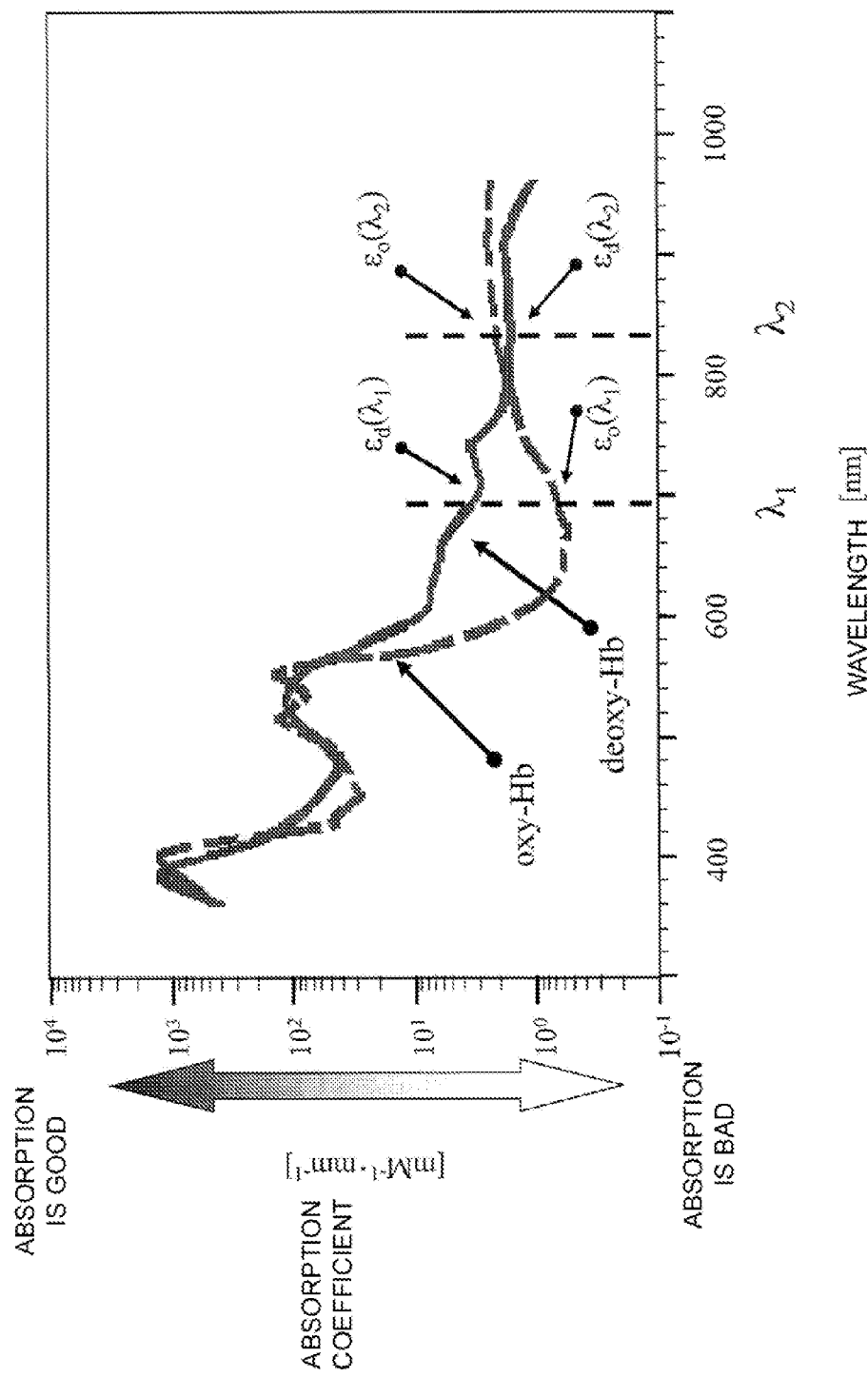
FIG. 2 is a graph illustrating a correspondence relationship between an irradiation wavelength and absorption coefficient values with respect to oxy Hb and deoxy Hb.

In Expression (1), the absorption coefficient values $\epsilon o(\lambda)$ and $\epsilon d(\lambda)$ of oxy Hb and deoxy Hb are known if irradiation wavelengths are determined since changes thereof with respect to the irradiation wavelengths are already known, as shown in FIG. 2. Accordingly, in Expression (1), since the unknowns are two of $\Delta(CoL)$ and $\Delta(CdL)$, it is possible to calculate the oxy Hb variation $\Delta(CoL)$ and the deoxy Hb variation $\Delta(CdL)$ from the following simultaneous equations (2a) and (2b), using beams ($\lambda 1$, $\lambda 2$) having two or more different wavelengths.

[Expression 2]

$$\Delta A(\lambda_1) = -\ln\left(\frac{I_{act}(\lambda_1)}{I_{base}(\lambda_1)}\right) = \varepsilon_o(\lambda_1)\Delta(C_oL) + \varepsilon_d(\lambda_1)\Delta(C_dL) \quad (2a)$$

$$\Delta A(\lambda_2) = -\ln\left(\frac{I_{act}(\lambda_2)}{I_{base}(\lambda_2)}\right) = \varepsilon_o(\lambda_2)\Delta(C_oL) + \varepsilon_d(\lambda_2)\Delta(C_dL) \quad (2b)$$

Specifically, the signal processing unit 34 calculates the oxy Hb variation $\Delta(CoL)$ and the deoxy Hb variation $\Delta(CdL)$ for each measurement point, using detection signals Ibase (1) and Iact ($\lambda 1$) of a wavelength light ($\lambda 1$) of the LDA 16 and detection signals Ibase ($\lambda 2$) and Iact ($\lambda 2$) of a wavelength light ($\lambda 2$) of the LDB 17 detected by the optical measurement unit 12, absorption coefficient values $\epsilon o(\lambda 1)$, $\epsilon d(\lambda 1)$, $\epsilon o(\lambda 2)$ and $\epsilon d(\lambda 2)$ of oxy Hb and deoxy Hb obtained in advance from FIG. 2, and Expressions (2a) and (2b).

On the other hand, in the LDA 16 and the LDB 17, if a temperature change or an optical output change occurs, a mode hopping phenomenon occurs, and thus, the wavelengths $\lambda 1$ and $\lambda 2$ are changed. If the wavelengths $\lambda 1$ and $\lambda 2$ are changed, the absorption coefficient values $\epsilon o(\lambda 1)$, $\epsilon d(\lambda 1)$, $\epsilon o(\lambda 2)$ and $\epsilon d(\lambda 2)$ are changed as is obvious from FIG. 2. Thus, if the signal processing unit 34 does not correct the absorption coefficient values used in calculation, deviation occurs in the calculated oxy Hb variation and deoxy Hb variation. Particularly, in some of the used wavelengths (for example, wavelength of 695 nm), inclination of the absorption coefficient value of each Hb is great. Thus, if wavelength correction is not performed, it is difficult to calculate the oxy Hb variation and the deoxy Hb variation with high accuracy.

Since the biological measuring device is a small device that is capable of simply measuring the Hb variation or the like without damaging an object with low restraint, it is possible to easily use the biological optical measurement instrument in hospitals or the like around the world from the tropics to cold latitudes, and it is assumed to use the biological optical measurement instrument in facilities or rooms where a temperature controller such as air-conditioning or heating is not provided. Thus, the width of usage temperature of the biological optical measurement instrument is very wide, which may cover a range of below-zero to 40° C. or higher. According to the usage temperature change of the biological optical measurement instrument, temperature changes in the LAD 16 and the LAD 17 occur.

Figure 3:
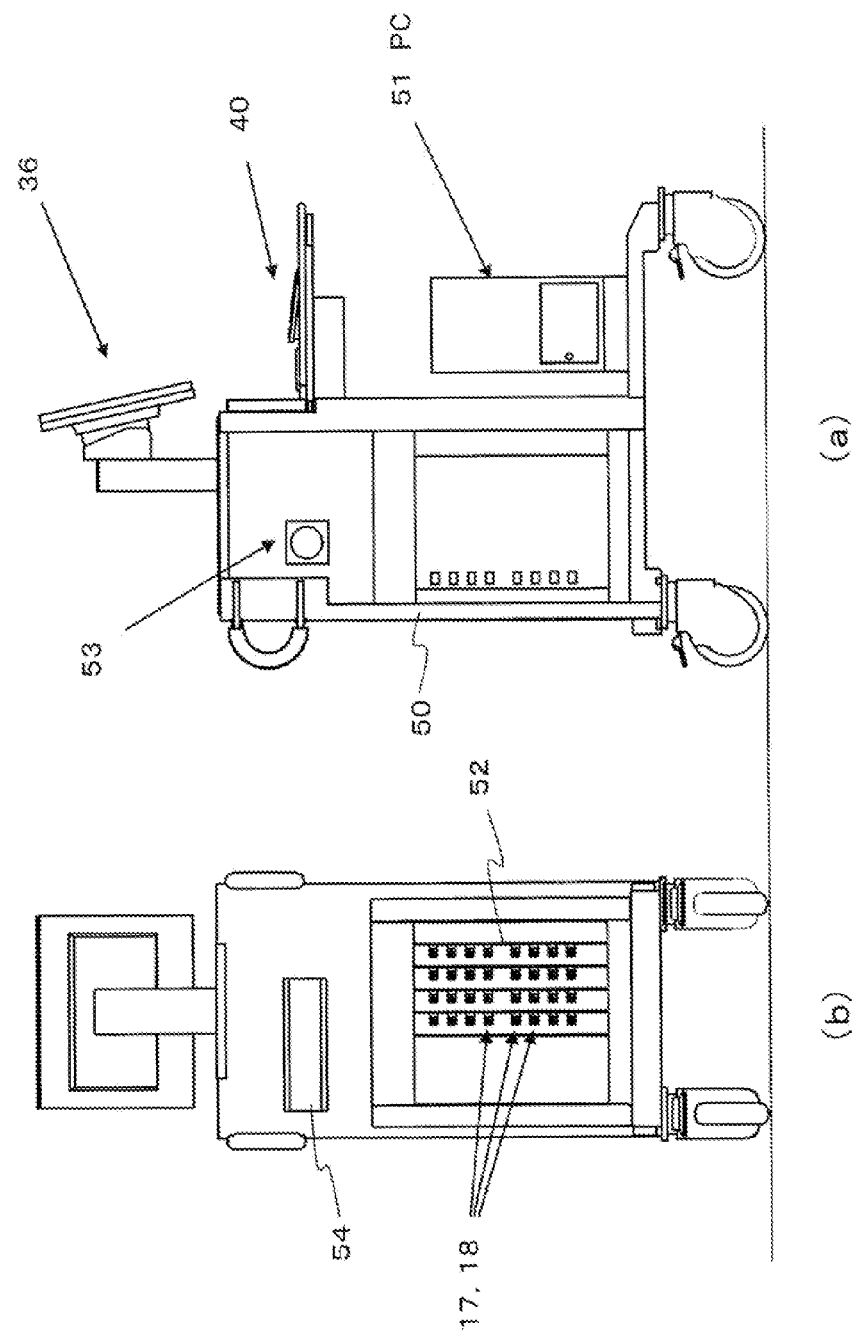
Figure 4:
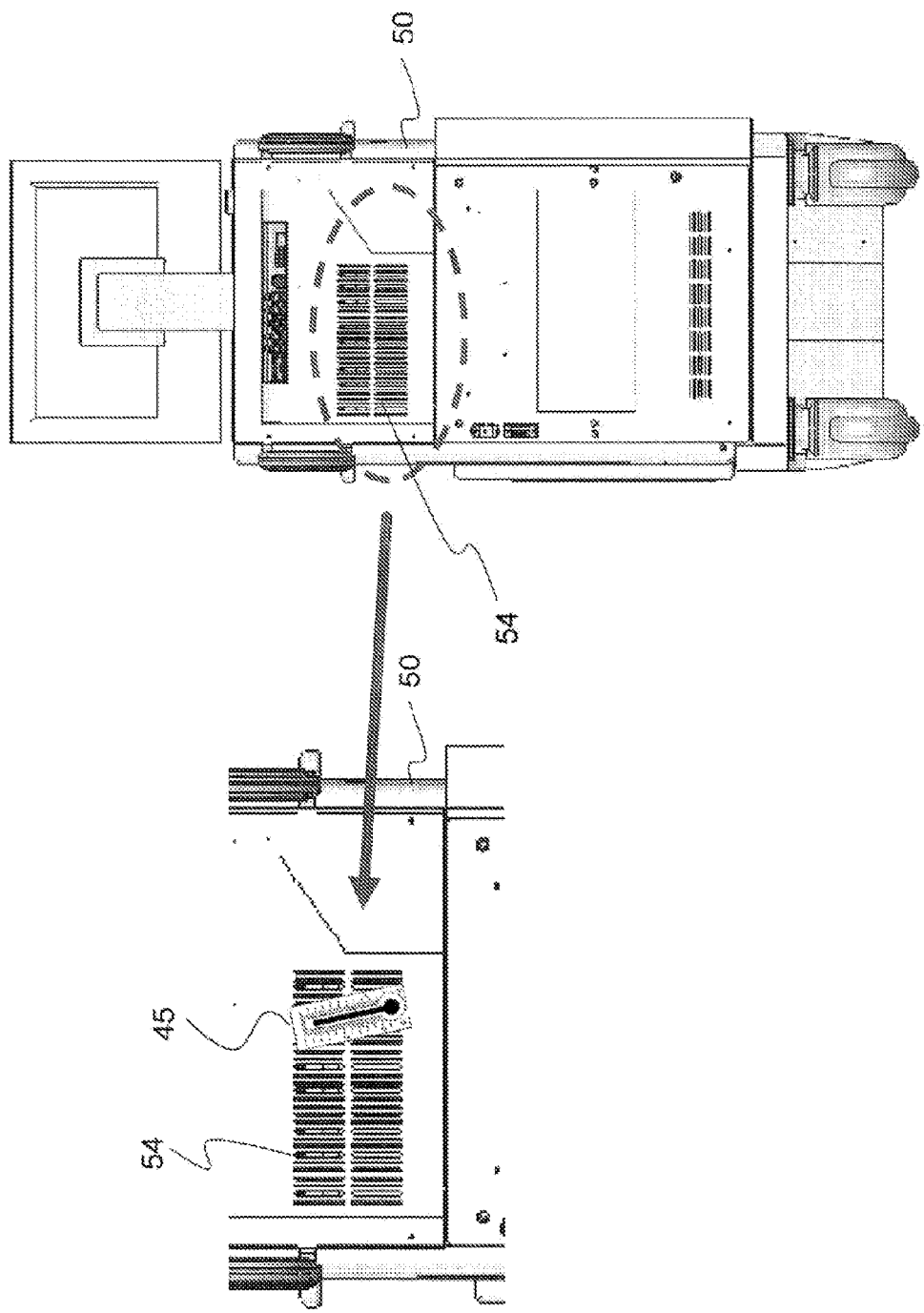
FIG. 4 shows a rear view of the casing of the biological optical measurement instrument in FIG. 1, and a partially enlarged view thereof.

An external appearance of the biological optical measurement instrument is shown in FIGS. 3(a), 3(b), and FIG. 4. FIGS. 3(a) and 3(b) are a side view and a rear view thereof in a state where a rear panel and a side panel of a casing 50 are partially opened so that the inside thereof can be seen from the outside. As shown in FIGS. 3(a) and 3(b) and FIG. 4, the device includes the casing 50 that accommodates the light source unit 10, the optical measurement unit 12 and the controller 14, the signal processing unit 34, the memory 38, and a memory built-in computer 51 that realizes the functions of the absorption coefficient correcting unit 44 and the like. For this reason, a plurality of substrates 52 mounted with the plurality of LDAs 16 and LDBs 17 and electronic circuits are adjacently accommodated in the casing 50. A fan 53 and an exhaust port 54 are provided in the casing 50. Air in the casing 50 is exhausted through the exhaust port 54, and thus, heat emitted by the plurality of the LDAs 16, the LDBs 17 and the like is exhausted.

According to the positional relationship between the exhaust port 54 and the fan 53, and the LDA 16 and the LDB 17, or according to the arrangement of the plurality of LDAs 16 and LDBs 17, distribution is generated in temperatures of the LDAs 16 and LDBs 17.

In the present embodiment, in consideration of the temperature distribution of the respective LDAs 16 and LDBs 17, temperatures of the LDAs 16 and the LDBs 17 are estimated according to a radiation temperature from all the LDAs 16 and the LDBs 17. Thus, the absorption coefficient values $\epsilon o(\lambda 1)$ and $\epsilon d(\lambda 1)$ and the absorption coefficient values $\epsilon o(\lambda 2)$ and $\epsilon d(\lambda 2)$ generated due to the wavelength variation are corrected. The correction is performed by operating the comparator 43, the absorption coefficient correcting unit 44, the memory 38, and the LD temperature detecting unit 42 as in the flow of FIG. 5.

Figure 5:
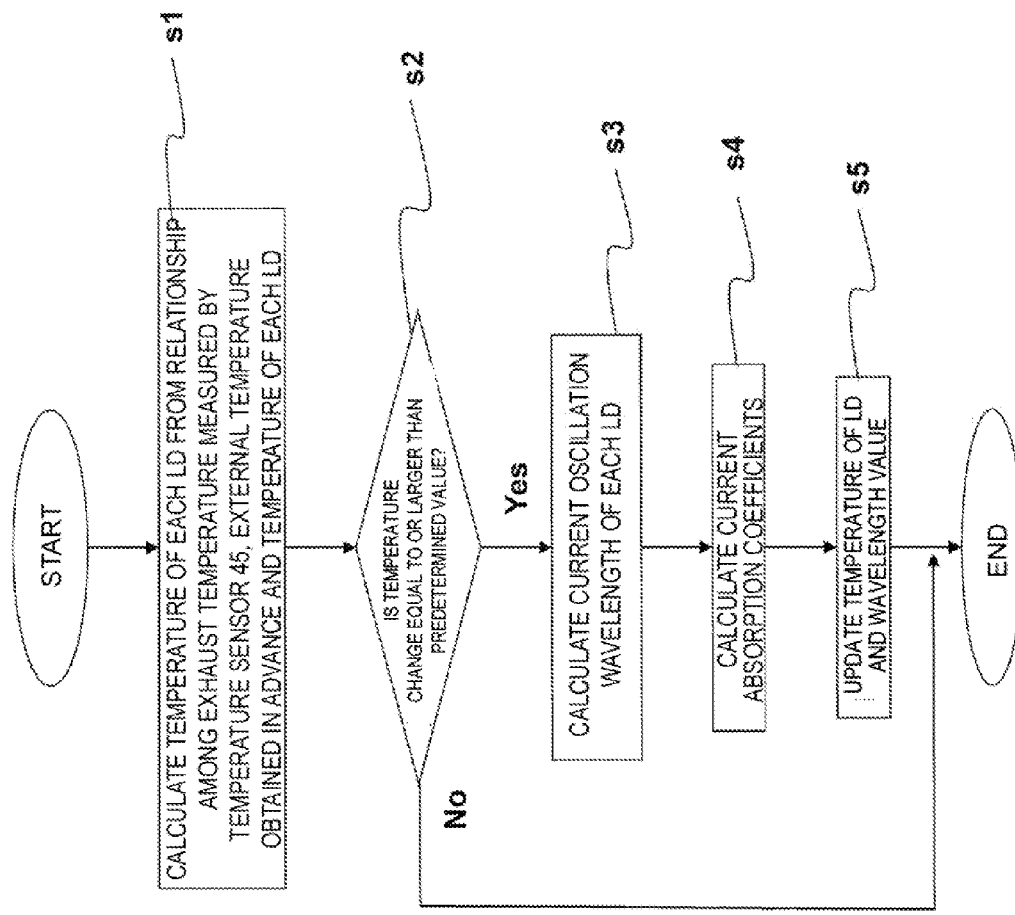
FIG. 5 is a flowchart illustrating an operation of correcting absorption coefficient values according to an exhaust temperature in the device according to the first embodiment.
Figure 6:
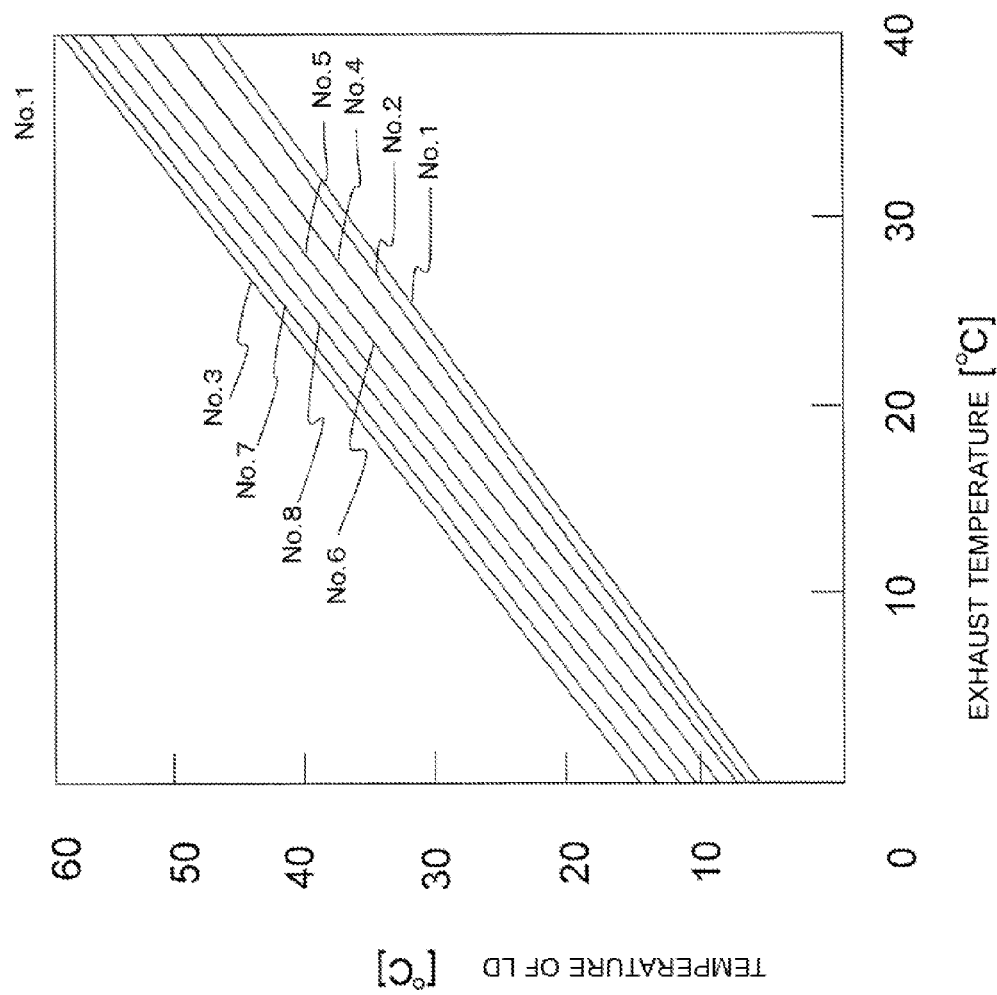
FIG. 6 is a graph illustrating a correspondence relationship between an exhaust temperature and a temperature of each LD in the first embodiment.
Figure 7:
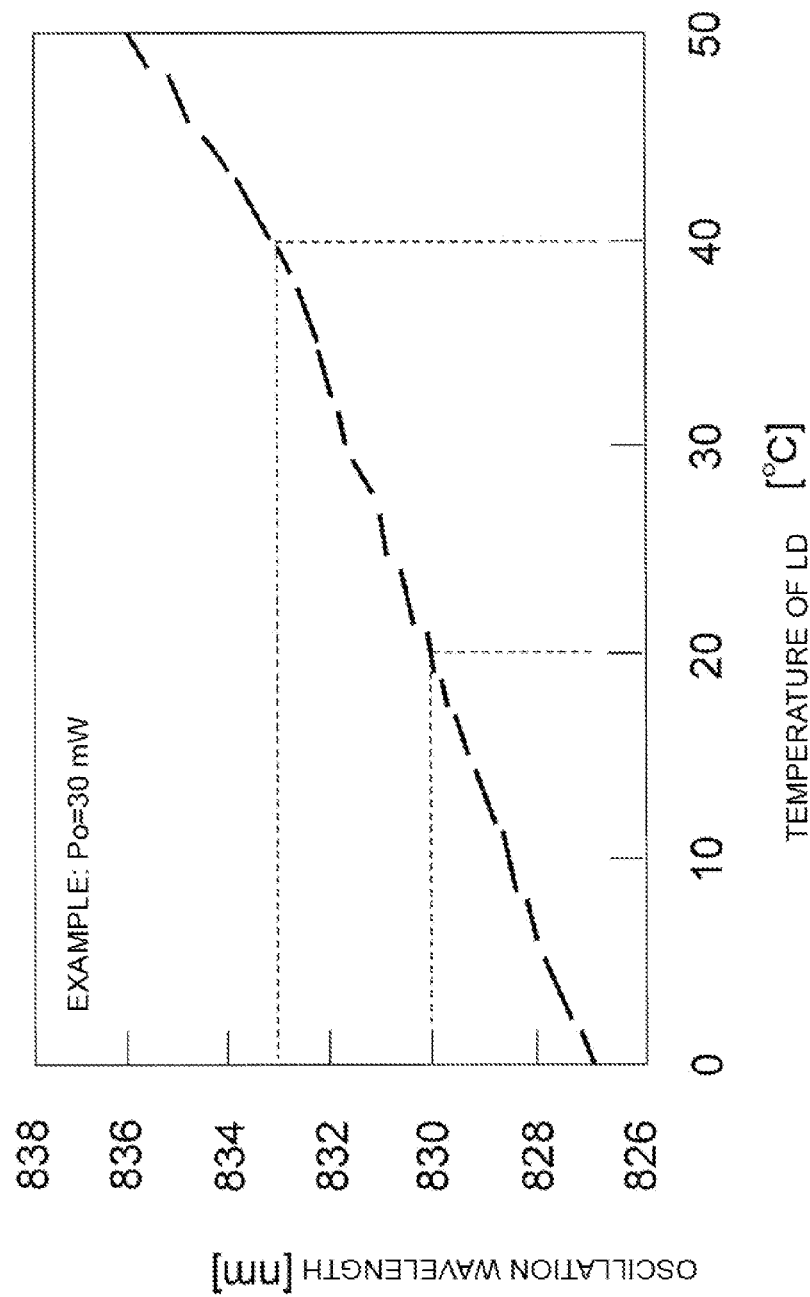
FIG. 7 is a graph illustrating a correspondence relationship between a temperature of an LD and an oscillation wavelength in the first embodiment.

In the memory 38, (1) specific temperatures of predetermined LDAs 16 and LDBs 17 (reference temperature, for example, 20° C.), (2) data indicating a correspondence relationship between a premeasured radiation temperature from all the LDAs 16 and the LDBs 17 detected by the temperature sensor 45 and a temperature of each of the LDAs 16 and the LDBs 17 as shown in FIG. 6, (3) data indicating a correspondence relationship between the premeasured temperature of each of the LDAs 16 and the LDBs 17 and an oscillation wavelength thereof as shown in FIG. 7, and (4) data indicating a correspondence relationship between a laser wavelength and absorption coefficient values of oxy Hb and deoxy Hb as shown in FIG. 2 are stored in advance. It is possible to store the data indicating the correspondence relationships of (2) to (4) described above in a graph form as shown in FIGS. 5, 7 and 2, or to store the data in a table form or a function form.

Data indicating the correspondence relationship between the temperature detected by one temperature sensor 45 and the temperature of each of the LDAs 16 and the LDBs 17 in (2) described above may be calculated in advance by installing a temperature sensor such as a thermocouple to each of the LDAs 16 and the LDBs 17, performing oscillation with a predetermined output (for example, 30 mW), and measuring an exhaust temperature detected by the temperature sensor 45 and the temperature of each of the LDAs 16 and the LDBs 17 while changing the temperature (FIG. 6). The installation position of the temperature sensor 45 is a predetermined specific position, for example, in the vicinity of the exhaust port 54 of the casing 50, as shown in FIG. 4. Thus, the temperature sensor 45 measures an exhaust temperature (including a temperature change), where an outdoor temperature is increased according to the radiation temperature of all the LDAs 16 and the LDBs 17. Further, a CPU or the like other than the LDs may be considered as a radiation source. In this description, since the radiation source includes only the plurality of LDs, the CPU or the like that may be another radiation source is partitioned from the LDs by a heat-shield (made of aluminum or the like) inside the casing, and thus, radiation from the CPU or the like hardly affects the exhaust of the plurality of LDs.

As described above, one temperature sensor 45 is installed to the exhaust port 54 in order to measure the exhaust temperature of the plurality of LDs, but the temperature sensor 45 may be installed to a radiation fin that transfers heat from the plurality of LDs, which achieves the same effect.

Further, although the temperatures of only eight LDs of No. 1 to No. 8 with respect to the exhaust temperature are shown in FIG. 6, but data with respect to all the LDs is measured in reality and is stored in the memory 38.

A correction operation of the absorption coefficient values will be specifically described with reference to the flow of FIG. 5.

(Step 1)

First, the LD temperature detecting unit 42 measures an exhaust temperature from an output of one temperature sensor 45, and calculates a temperature of each of the LDAs 16 and the LDBs 17 referring to the data (FIG. 6) indicating the correspondence relationship between the exhaust temperature and the temperature of each of the LDAs 16 and the LDBs 17 in (2) described above stored in the memory 38. The calculated temperature is stored in the memory 38.

(Step 2)

The comparator 43 compares the temperature of each of the LDAs 16 and the LDBs 17 calculated in step 1 by the LD temperature detecting unit 42 with the specific temperature (reference temperature) of (1) described above stored in the memory. In a case where there is an LD in which the temperature difference is larger than a predetermined value, the comparator 43 performs correction of the absorption coefficient values in steps 3 and 4, and in a case where the temperature differences of all the LDs are within the predetermined value, the procedure ends as it is. The predetermined value is set to ±5° C., for example. As shown in FIG. 7, since the wavelength is changed by about 1 nm due to the change of 5° C., it is possible to set an allowable range up to about ±5° C.

(Step 3)

In step 2, in a case where there is an LD in which the current temperature is higher than the reference temperature by ±5° C. or more, the absorption coefficient correcting unit 44 calculates an oscillation wavelength at the current temperature with respect to each of the LDAs 16 and the LDBs 17, referring to the data (FIG. 7) indicating the correspondence relationship between the temperature of each of the LDAs 16 and the LDBs 17 and the oscillation wavelength in (3) described above stored in the memory 38.

(Step 4)

Further, the absorption coefficient correcting unit 44 calculates absorption coefficient values $\epsilon 0$ and $\epsilon d$ with respect to a current wavelength of each of the LDAs 16 and the LDBs 17, referring to the data (FIG. 2) indicating the correspondence relationship between the laser wavelength and the absorption coefficient values of oxy Hb and deoxy Hb in (4) described above stored in the memory 38. The calculated absorption coefficient values are transmitted to the signal processing unit 34 through the controller 14. Thus, the signal processing unit 34 may calculate an oxyhemoglobin (oxy Hb) concentration change and a deoxyhemoglobin (deoxy Hb) concentration change using the corrected absorption coefficient values for each of the LDAs 16 and the LDBs 17.

(Step 5)

The absorption coefficient correcting unit 44 stores the current oscillation wavelength calculated for each of the LDAs 16 and the LDBs 17 in the memory. The memory 38 stores the current oscillation wavelength, the temperature of an LD that has the largest temperature difference from the reference value among the temperatures of the LDs stored in step 1, and a difference between the initial value and the current value of the wavelength of the LD, as a table. A table in FIG. 8 is displayed on the display 36 by the controller 14, and is reported to an operator.

Next, the overall operation of the biological optical measurement instrument will be described with reference to the flow in FIG. 9. The operation is realized as the controller 14 controls the operations of the respective units.

(Step 101)

First, if the operator turns on a switch of the biological optical measurement instrument, the controller 14 oscillates the LDAs 16 and the LDBs 17 of the light source unit 10 to perform warming-up for a predetermined time. Thus, the operation of the LDs is stabilized. After the predetermined warming-up time elapses, an indication for notifying the operator of the fact that the device is in a measurable state is displayed on the display 36.

(Step 102)

The controller 14 displays an indication for encouraging the operator to mount the probe holder 23 to the object 22 on the display 36. Thus, the operator mounts the probe holder 23 at a measurement portion of the object 22.

(Step 103)

The controller 14 displays a screen for receiving setting of various parameter values or selection of a measuring method from the operator on the display 36, to thereby encourage the operator to perform the setting. If the operator inputs a setting value or the like from the input and output unit 40, the controller 14 receives the setting value or the like.

(Step 104)

The controller 14 detects detection signals of the wavelength of the LDA 16 and the wavelength of the LDB 17 in each measurement point, and performs gain adjustment from the output of the optical measurement unit 12. That is, in a case where there is a measurement point of which the intensity of the detection signal is weak, the operator is encouraged to adjust the position of the probe holder, or is encouraged to adjust the gain so as to adjust an optical output of the LD to obtain a predetermined detection intensity.

(Step 105)

Next, the controller 14 performs correction of the absorption coefficient values. The correction of the absorption coefficient values is performed by executing the above-described flow in FIG. 5. Thus, the controller 14 calculates the absorption coefficient values $\epsilon\theta$ and $\epsilon d$ with respect to the current wavelength of each of the LDAs 16 and the LDBs 17 that is changed according to the temperature at which the biological optical measurement instrument is disposed and the temperatures of the LDs, and sets the result in the signal processing unit 34.

(Step 106)

The controller 14 irradiates the measurement portion of the object 22 with light from the light source 10, and detects transmitted light in each measurement point of the measurement portion by the optical measurement unit 12 to acquire a detection signal. The measurement operation is as described above.

(Steps 107 and 108)

In a case where a predetermined time (for example, five minutes) elapses during the measurement, or in a case where the exhaust temperature detected by the temperature sensor 45 varies by a predetermined temperature (for example, 2° C.) or higher from the start of the measurement, the controller 14 executes steps 1 to 4 in FIG. 5 (step 107). Thus, in a case where any temperature of the respective LDs calculated in step 2 varies more than a predetermined allowable width, in a case where any oscillation wavelength of the respective LDs calculated in step 3 varies more than a predetermined allowable width, or in a case where there is an LD in which the absorption coefficient values calculated in step 4 vary more than a predetermined allowable width, an alarm that notifies the operator of the fact that measurement accuracy deteriorates due to a temperature change is displayed on the display 36, in step 108. Thus, the operator may determine whether to continue or stop the measurement.

(Step 109)

The operator inputs continuation/stop of the measurement to the input and output unit 40. The controller 14 receives an input of the input and output unit 40, and returns the procedure to step 107 and continues the measurement in the case of continuation and returns the procedure to step 104 and performs gain adjustment in the case of stop.

(Step 110)

If the measurement ends, the signal processing unit 34 calculates the oxy Hb variation, the deoxy Hb variation or the like using the detection signal obtained in the measurement and the absorption coefficient values after correction set in step 105. This calculation method is as described above. The calculation result is generated as an image of a display method desired by the operator, and is displayed on the display 36.

As described above, in the biological optical measurement instrument according to the present embodiment, the absorption coefficient correcting unit 44 calculates the adsorption coefficient values corresponding to the output of the temperature sensor 45 for each of the plurality of light emitting elements, referring to the data indicating the correspondence relationship between the exhaust temperature calculated in advance for each of the plurality of light emitting elements and the absorption coefficient values that vary according to the temperature change in the light emitting elements, using the detection output of the exhaust temperature of the temperature sensor 45. Thus, it is possible to calculate the temperature change in the LD that is caused due to any oscillation wavelength of the plurality of light emitting elements by the change in the exhaust temperature for each of the plurality of LDs, to calculate the wavelength for each LD, and to correct the absorption coefficient values $\epsilon\theta$ and $\epsilon d$. Accordingly, even in a case where the biological optical measurement instrument is used under the condition of various outdoor temperatures that significantly affect the exhaust temperature (for example, from the tropics to cold latitudes), it is possible to calculate information in a living body with high accuracy.

In step 108, only the alarm is given, but a configuration in which a process of reducing the temperature change is performed in addition to the alarm may be used. For example, in a case where the temperature is increased, it is possible to increase the rotational speed of the fan 53 to cool the LDs, or in a case where the temperature is decreased, it is possible to heat the LDs by a heater that is disposed in the vicinity of the LDs in advance.

Further, in the present embodiment, in steps 1 to 4 in FIG. 5, the absorption coefficient values are calculated from the exhaust temperature in three steps of exhaust temperature→temperature of each LD→wavelength of each LD→absorption coefficient values. With such a configuration, in a case where an LD is exchanged, it is sufficient if the data temperature (FIG. 7) indicating the correspondence relationship between the temperature of the LD and the oscillation wavelength in (3) described above stored in the memory 38 is stored with only respect to the exchanged LD, thereby making it possible to easily cope with the LD exchange.

Here, the present embodiment is not limited to the configuration in which the absorption coefficient values are calculated from the exhaust temperature in three steps. By calculating the correspondence relationship between the exhaust temperature and the wavelength of the LD in advance and storing the data in the memory 38 for each LD, it is possible to use a two-step configuration of directly calculating the wavelength of the LD from the exhaust temperature and calculating the absorption coefficient values from the wavelength of the LD. Further, by calculating the correspondence relationship between the exhaust temperature and the absorption coefficient values for each LD, it is also possible to calculate the absorption coefficient values in one step.

Second Embodiment

Figure 9:
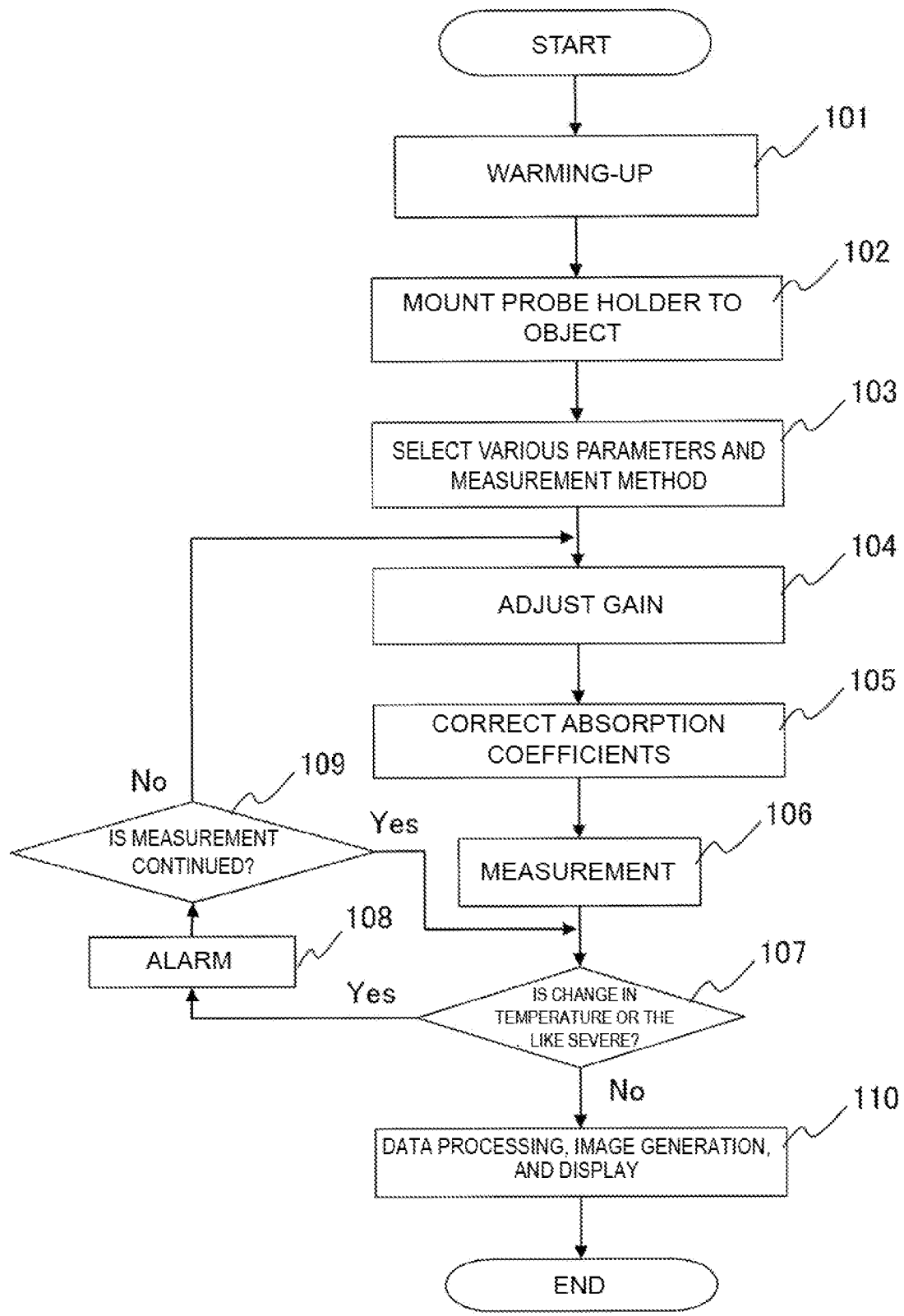
FIG. 9 is a flowchart illustrating an overall operation of the biological optical measurement instrument according to the first embodiment.
Figure 10:
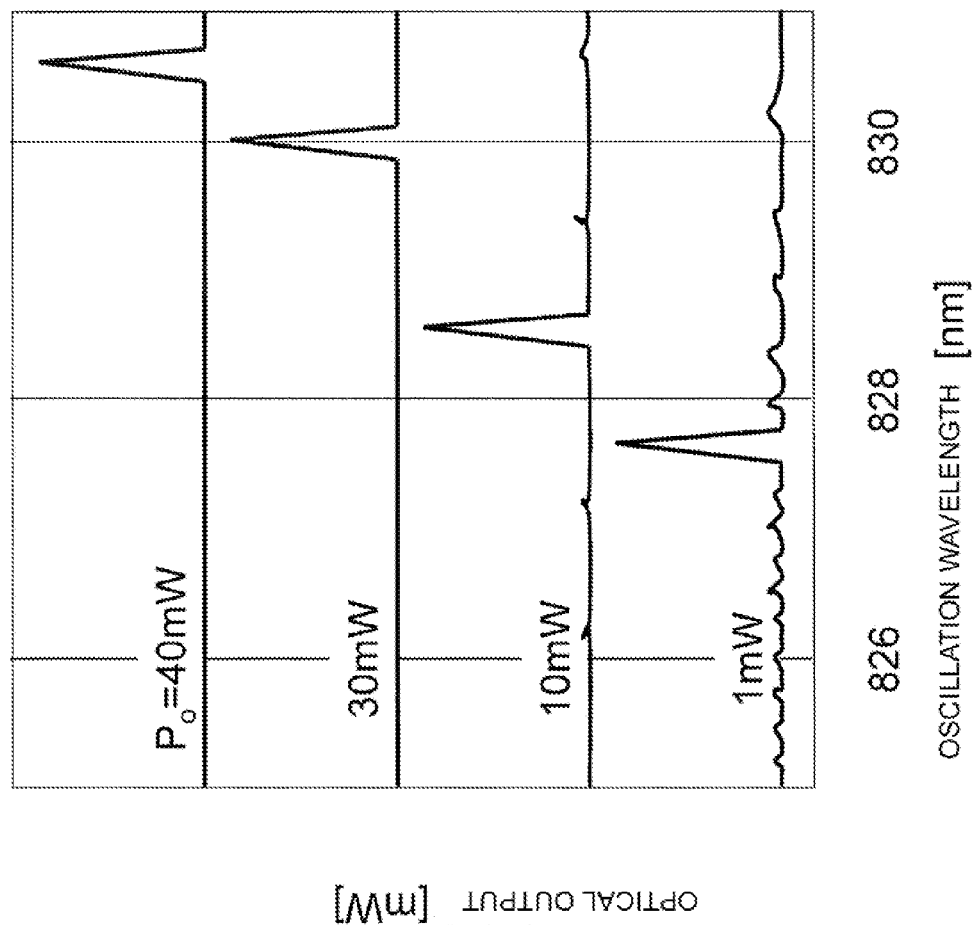
FIG. 10 is a graph illustrating an oscillation wavelength that is changed according to an optical output of an LD in a second embodiment.

In the biological optical measurement instrument of the first embodiment, in a case where there is a problem of propagation efficiency reduction due to damage or the like in the optical fiber 20 of the light source unit 10 in step 104 in FIG. 9 and the optical output of the LD is adjusted for gain adjustment, the mode hopping phenomenon may occur according to change in the output of the LD as shown in FIG. 10, and thus, the wavelength may be changed.

Thus, in a second embodiment, in a case where the optical output of the LD is adjusted in gain adjustment, a function of correcting absorption coefficient values according to a wavelength change due to the output change in the LD is added.

Figure 11:
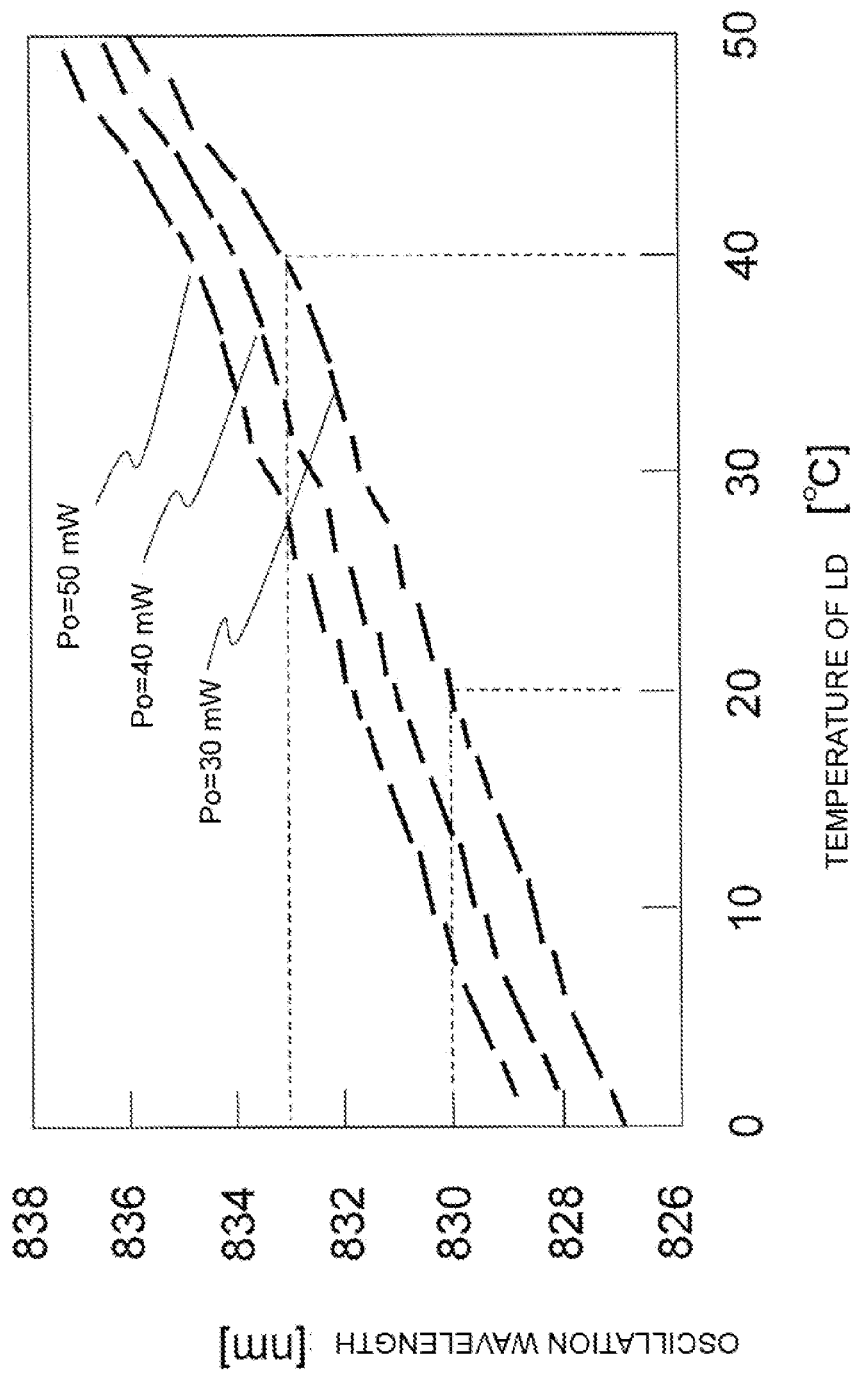
FIG. 11 is a graph illustrating a correspondence relationship between an optical output of an LD, a temperature of the LD and an oscillation wavelength in the second embodiment and a third embodiment.

Specifically, in the present embodiment, in place of the data indicating the correspondence relationship between the temperature of the LD and the oscillation wavelength in FIG. 7, as shown in FIG. 11, the data indicating the correspondence relationship between the temperature of the LD and the oscillation wavelength for each optical output of the LD is stored in advance in the memory 38. Thus, in a case where the optical output of the LD is adjusted for gain adjustment in step 104 in FIG. 9, it is possible to calculate the oscillation wavelength according to the output of the LD, referring to the data in FIG. 11 in step 3 in FIG. 5 in correction of the absorption coefficient values in step 105. Accordingly, it is possible to correct the absorption coefficient values with high accuracy even in a case where the output of the LD is adjusted.

Figure 12:
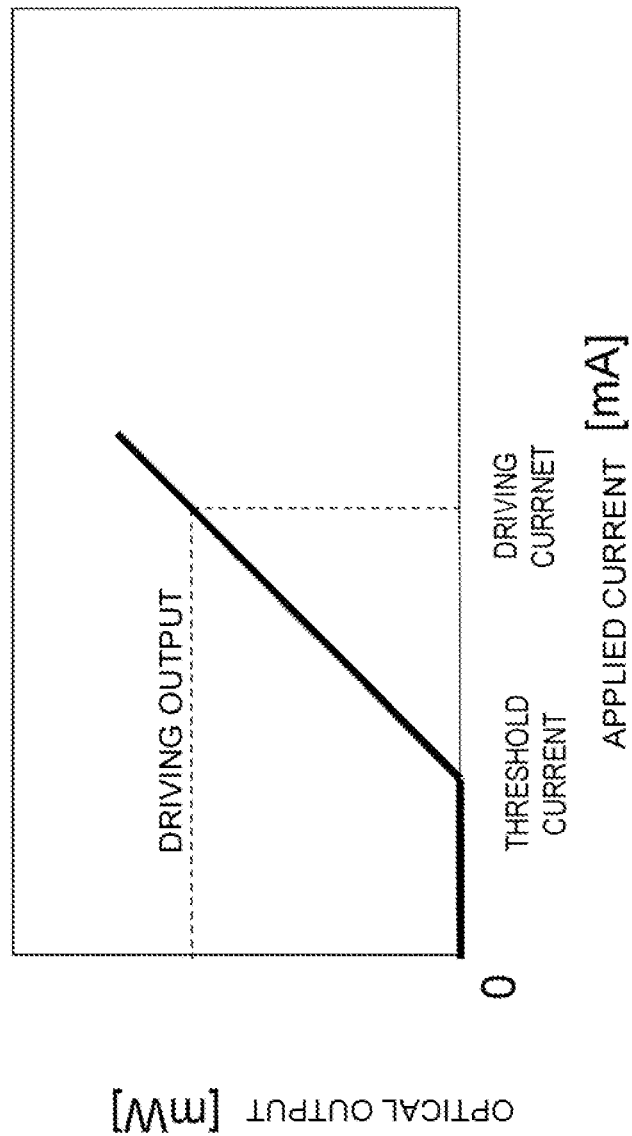
FIG. 12 is a graph illustrating a correspondence relationship between electric current (driving current) applied to an LD and an optical output in the second and third embodiments.

If the optical output of the LD is equal to or higher than a light emitting threshold current as shown in FIG. 12, the optical output is proportional to a driving current, and it is thus possible to calculate the optical output using the driving current supplied from the optical module 18 to the LD of which the gain is adjusted and the correspondence relationship between the optical output and the driving current in FIG. 12 that is obtained in advance. Other configurations are the same as in the first embodiment.

Here, in the second embodiment, even though the optical output of the LD is adjusted for gain adjustment, it is assumed that the temperature of the LD is not changed. This is because in a case where the temperature of the LD is changed according to the adjustment in the optical output of the LD, it is necessary to prepare the data indicating the correspondence relationship between the exhaust temperature and the temperature of each LD in FIG. 6 for each optical output of the LD. Thus, it is possible to measure in advance the data indicating the correspondence relationship between the exhaust temperature and the temperature of each LD in FIG. 6 for each output of the LD and to store the result in the memory 38. By referring to this assumption in step 1 in FIG. 5, it is possible to correct the absorption coefficient values using the second embodiment even in a case where the temperature of the LD is changed according to the adjustment in the optical output of the LD.

Third Embodiment

In a third embodiment, a biological optical measurement instrument that has a function for correcting the absorption coefficient values corresponding to the wavelength change due to the adjustment in the optical output of the LD in maintenance will be described.

The maintenance corresponds to maintenance in which it is confirmed whether a predetermined light intensity exits from an exiting end of the irradiation optical fiber 20 and the optical outputs of the LDAs 16 and the LDBs 17 are adjusted in a case where the predetermined light intensity is not obtained. Here, the maintenance is performed in a case where the LDAs 16 and the LDBs 17 are not damaged.

In the present embodiment, in a case where the adjustment in the optical output of each LD is performed in maintenance, the function for correcting the absorption coefficient values is provided to cope with occurrence of the wavelength change in the LD.

Figure 13:
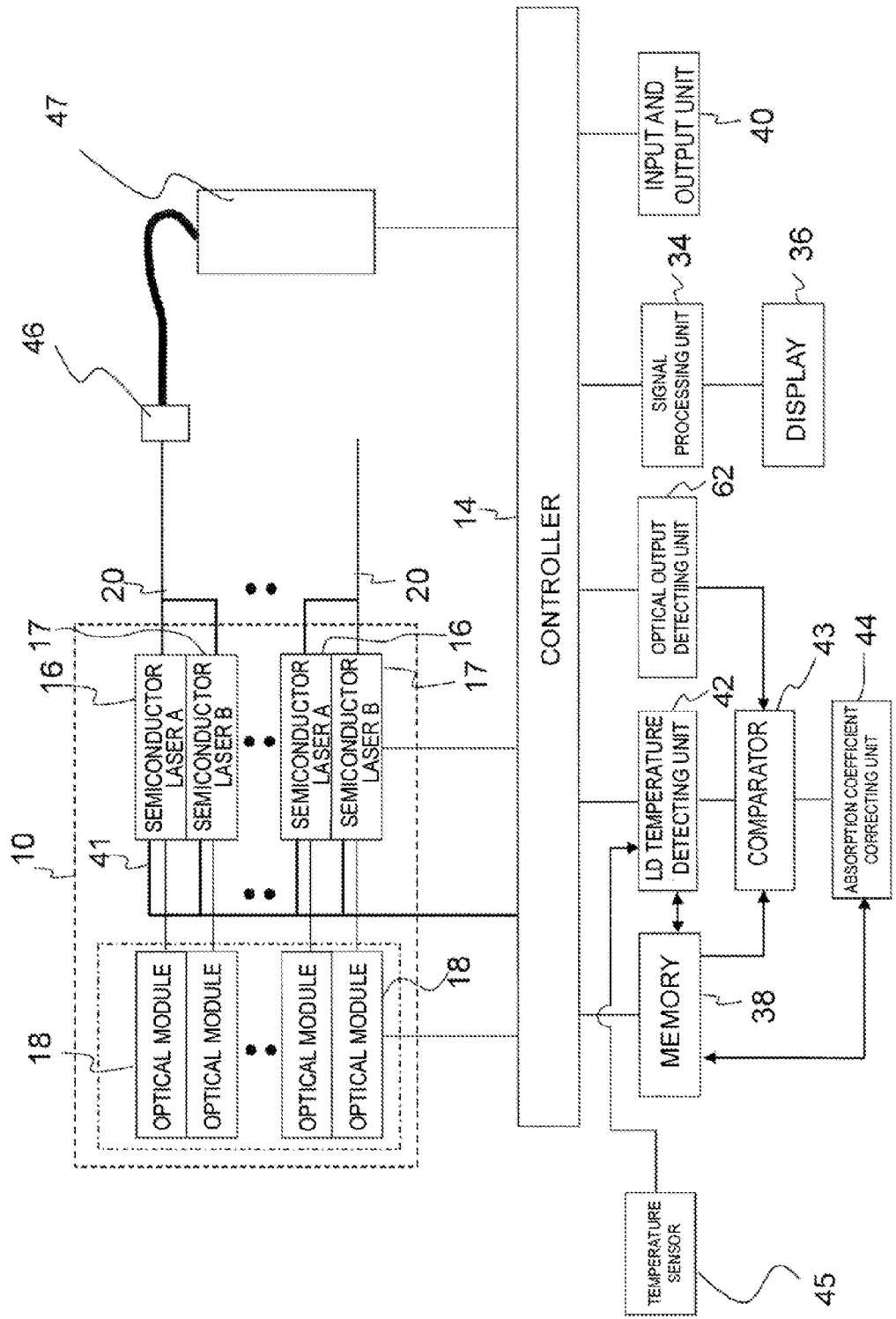
FIG. 13 is a block diagram illustrating a configuration of a biological optical measurement instrument according to the third embodiment in maintenance.

Specifically, the biological optical measurement instrument of the present embodiment includes an optical output detecting unit 62 that is used in maintenance, as shown in FIG. 13. Other configurations are the same as in the device of the first embodiment. The optical output detecting unit 62, the comparator 43, the absorption coefficient correcting unit 44 and the memory 38 are operated in maintenance as the flow in FIG. 14, and thus, the absorption coefficient values are corrected according to the optical output.

As shown in FIG. 13, in maintenance, an optical sensor 46 is installed to the exiting end of the irradiation optical fiber 20 of the light source 10, and the light intensity is measured by an optical power meter 47. Further, thermocouples 41 are respectively connected to all the LDAs 16 and the LDBs 17, and the controller 14 receives the outputs.

In the memory 38, (1) predetermined optical outputs of predetermined LDAs 16 and LDBs 17 (30 mW, for example), (2) data indicating a correspondence relationship between a premeasured applied current (driving current) and the optical output as shown in FIG. 12, (3) data indicating a correspondence relationship between the premeasured optical output of each of the LDAs 16 and the LDBs 17 and an oscillation wavelength thereof as shown in FIG. 11, and (4) data indicating a correspondence relationship between a laser wavelength and absorption coefficient values of oxy Hb and deoxy Hb as shown in FIG. 2 are stored in advance. It is possible to store the data indicating the correspondence relationships of (2) to (4) described above in a graph form as shown in FIGS. 11, 12 and 2, or to store the data in a table form or a function form.

Figure 14:
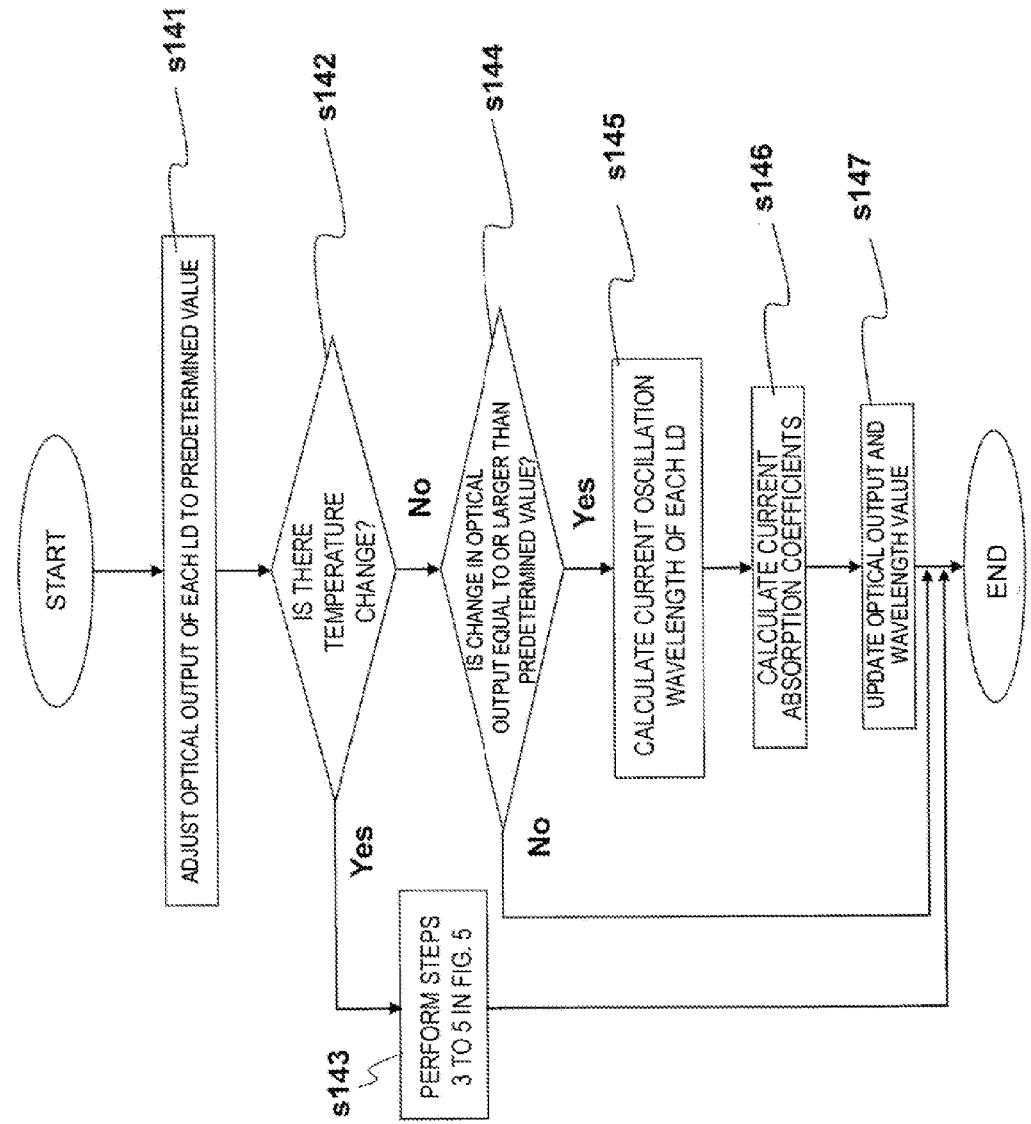
FIG. 14 is a flowchart illustrating a correction operation of absorption coefficient values in maintenance in the third embodiment.

The correction operation of the absorption coefficient values in maintenance will be described in detail with reference to the flow in FIG. 14.

(Step 141)

An optical output of a tip end portion of the irradiation optical fiber 20 is measured using the optical sensor 46 and the optical power meter 47, and in a case where the measured optical output is deviated from a predetermined value, an electric current applied from the optical module 18 to the LD to which the irradiation optical fiber 20 is connected is adjusted under the control of the controller 14 to obtain a predetermined optical output.

(Step 142)

The controller 14 confirms whether a temperature change occurs in the adjusted LD before and after the optical output is adjusted in step 141, using the thermocouple 41.

(Step 143)

In a case where the temperature change is larger than a predetermined temperature (for example, ±5° C.) in step 141, the controller 14 performs steps 3 to 5 in FIG. 5 to calculate a wavelength change due to the temperature change, to then correct the absorption coefficient values.

(Step 144)

In step 141, in a case where the temperature change is equal to or lower than the predetermined temperature, the optical output detecting unit 62 imports the driving currents before and after adjustment in the adjusted LD from the optical module 18, and calculates the optical outputs respectively, referring to the data (FIG. 12) indicating the correspondence relationship between the applied current (driving current) and the optical output of (2) described above in the memory 38. In a case where the optical output difference between before and after adjustment is smaller than a predetermined value (for example, ±10 mW), the optical output difference is in an allowable range, and thus, correction of the absorption coefficient values is not performed, and then the procedure ends. Since the mode hopping due to the optical output is not severe compared with the temperature change, the allowance of about ±10 mW is given. In a case where the optical output difference between before and after adjustment is equal to or larger than the predetermined value, the procedure proceeds to step 145.

(Step 145)

The absorption coefficient correcting unit 44 receives the optical output after adjustment in the LD of which the optical output is adjusted by the predetermined value or higher from the optical output detecting unit 62, and receives the temperature of the LD after adjustment from the thermocouple 41 through the controller 14. Further, the absorption coefficient correcting unit 44 calculates a current oscillation wavelength, referring to the data (FIG. 11) indicating the correspondence relationship among the optical output and temperature of each of the LDAs 16 and the LDBs 17 of (3) described above stored in the memory 38 and the oscillation wavelength thereof.

(Step 146)

Further, the absorption coefficient correcting unit 44 calculates absorption coefficient values $\epsilon 0$ and $\epsilon d$ with respect to a current wavelength of the LD of which the optical output is adjusted, referring to the data (FIG. 2) indicating the correspondence relationship between the laser wavelength and the absorption coefficient values of oxy Hb and deoxy Hb in (4) described above stored in the memory 38. The calculated absorption coefficient values are transmitted to the signal processing unit 34 through the controller 14. Thus, the signal processing unit 34 may calculate an oxy Hb concentration change and a deoxy Hb concentration change using the corrected absorption coefficient values for each of the LDAs 16 and the LDBs 17.

(Step 147)

The absorption coefficient correcting unit 44 stores the calculated oscillation wavelength in the memory 38. As shown in FIG. 15, the current oscillation wavelength of each LD, the optical output after adjustment in the adjusted LD and the wavelength change value (wavelength difference between before and after adjustment) are stored as a table in the memory 38. A table in FIG. 15 is displayed on the display 36 by the controller 14, and is reported to an operator.

Operations such as correction of the absorption coefficient values according to the temperature in measurement are the same as in the first embodiment, and thus, description thereof will not be repeated.

According to the biological optical measurement instrument according to the above-described third embodiment, it is possible not only to correct the absorption coefficient values according to the temperature in measurement, but also to correct the absorption coefficient values even in a case where the optical output is adjusted in maintenance. Accordingly, it is possible to calculate biological information such as oxy Hb or deoxy Hb with high accuracy, using the absorption coefficient values corresponding to the current wavelength of irradiated light with high accuracy.

In the third embodiment, with respect to the LD in which the temperature change occurs by the adjustment in the optical output in steps 142 and 143, when correction of the absorption coefficient values is performed in the flow in FIG. 5 according to the temperature change in measurement, it is normally necessary to prepare the data indicating the correspondence relationship between the exhaust temperature and the temperature of the LD in FIG. 6 according to the temperature after adjustment of the optical output. Thus, it is also possible to measure in advance the data indicating the correspondence relationship between the exhaust temperature and the temperature of each LD in FIG. 6 for each LD output and to store the data in the memory 38. By referring to the above description in step 1 in FIG. 5, it is possible to correct the absorption coefficient values according to the third embodiment even in a case where the temperature of the LD is changed according to the adjustment in the optical output of the LD.

REFERENCE SIGNS LIST

10 LIGHT SOURCE
12 OPTICAL MEASUREMENT UNIT
14 CONTROLLER
16 SEMICONDUCTOR LASER (LD) A
17 SEMICONDUCTOR LASER (LD) B
18 OPTICAL MODULE
20 IRRADIATION OPTICAL FIBER
22 OBJECT
23 PROBE HOLDER
26 DETECTION OPTICAL FIBER
28 PHOTOELECTRIC TRANSDUCER
30 LOCK-IN AMPLIFIER
32 A/D CONVERTER
34 SIGNAL PROCESSING UNIT
36 DISPLAY
38 MEMORY
40 INPUT AND OUTPUT UNIT
41 THERMOCOUPLE
42 LD TEMPERATURE DETECTING UNIT
43 COMPARATOR
44 ABSORPTION COEFFICIENT CORRECTING UNIT
45 TEMPERATURE SENSOR
46 OPTICAL SENSOR
47 OPTICAL POWER METER
62 OPTICAL OUTPUT DETECTING UNIT

The invention claimed is:

1. A biological optical measurement instrument comprising:
a plurality of light emitting elements that emit light of a predetermined wavelength;
a single temperature sensor that detects an exhaust temperature exhausted from a casing accommodating the plurality of light emitting elements;
a light guide configured to guide the light of the plurality of light emitting elements to an object for irradiation;
a controller configured to receive a setting for an oscillation wavelength of light that is emitted by the plurality of light emitting elements;
an optical detector configured to measure a transmitted light intensity in a plurality of measurement points of the object;
a memory that stores
a first relation that indicates a correspondence relationship between the exhaust temperature detected by the single temperature sensor and a temperature of each of the plurality of light emitting elements,
a second relation that indicates a correspondence relationship between the temperature of each of the plurality of light emitting elements and the oscillation wavelength, and
a third relation that indicates a correspondence relationship between the oscillation wavelength and an absorption coefficient value of a notable substance inside the object; and
a processor configured to
(a) calculate the temperature of each of the plurality of light emitting elements based on the exhaust temperature detected by the temperature censor and the first relation,
(b) calculate the oscillation wavelength for each of the plurality of light emitting elements based on the temperature of each of the plurality of light emitting elements calculated by step (a) and the second relation, and
(c) calculate the absorption coefficient value of the oscillation wavelength calculated by step (b) to the notable substance inside the object based on the oscillation wavelength and the third relation.

2. The biological optical measurement instrument according to claim 1, further comprising:
an alarm configured to generate an alarm in a case where a parameter varies more greatly than a predetermined variation width during measurement of the transmitted light intensity by the optical detector.

3. The biological optical measurement instrument according to claim 2,
wherein the parameter is the exhaust temperature detected by the temperature sensor.

4. The biological optical measurement instrument according to claim 2,
wherein the parameter is the absorption coefficient value.

5. The biological optical measurement instrument according to claim 1, further comprising:
an alarm configured to generate an alarm in a case where any one of the oscillation wavelengths of the plurality of light emitting elements varies more greatly than a predetermined variation width during measurement of the transmitted light intensity by the optical detector.

6. The biological optical measurement instrument according to claim 1, wherein:
the controller is configured to adjust an optical output of the plurality of light emitting elements so that the intensity of the light with which the object is irradiated by the light guide becomes a predetermined intensity,
the processor is configured to correct the absorption coefficient value corresponding to each of the plurality of light emitting elements according to the optical output, and
the processor is configured to calculate the absorption coefficient value corresponding to the optical output for each of the plurality of light emitting elements, referring to data indicating a correspondence relationship between an optical output calculated in advance for each of the plurality of light emitting elements and the absorption coefficient value that varies according to a wavelength variation due to an optical output change in the light emitting elements.

7. A method of operating a biological optical measurement instrument, comprising:
irradiating an object with light of a predetermined wavelength from a plurality of light emitting elements;
measuring a transmitted light intensity in a plurality of measurement points of the object;
detecting, with a single temperature sensor, an exhaust temperature exhausted from a casing accommodating the plurality of light emitting elements therein;
storing, via a memory,
a first relation that indicates a correspondence relationship between the exhaust temperature of the plurality of light emitting elements detected by the single temperature sensor and a temperature of each of the plurality of light emitting elements,
a second relation that indicates a correspondence relationship between the temperature of each of the plurality of light emitting elements and an oscillation wavelength of light that is emitted by the plurality of light emitting elements, and
a third relation that indicates a correspondence relationship between the oscillation wavelength and an absorption coefficient value of a notable substance inside the object; and
via a processor
(a) calculating the temperature of each of the plurality of light emitting elements based on the exhaust temperature detected by the single temperature sensor and the first relation,
(b) calculating the oscillation wavelength for each of the plurality of light emitting elements based temperature of each of the plurality of light emitting elements calculated by step (a) and the second relation, and
(b) calculating the absorption coefficient of the oscillation wavelength calculated by step (b) and the third relation.

8. The method according to claim 7, further comprising:
adjusting the optical output of the light emitting elements so that the intensity of the light with which the object is irradiated becomes a predetermined value,
wherein in a case where the optical output is adjusted, the absorption coefficient value corresponding to the optical output is corrected for each of the plurality of light emitting elements, referring to data indicating a correspondence relationship between an optical output calculated in advance for each of the plurality of light emitting elements and the absorption coefficient value that varies according to a wavelength variation due to an optical output change of the light emitting elements.

* * * * *